(12) United States Patent
Sakamoto et al.

(10) Patent No.: US 8,603,938 B2
(45) Date of Patent: Dec. 10, 2013

(54) METHOD FOR PREPARING CATALYST

(75) Inventors: Toru Sakamoto, Wakayama (JP); Taku Mimura, Wakayama (JP)

(73) Assignee: Kao Corporation, Tokyo (JP)

( * ) Notice: Subject to any disclaimer, the term of this patent is extended or adjusted under 35 U.S.C. 154(b) by 170 days.

(21) Appl. No.: 13/062,823

(22) PCT Filed: Sep. 10, 2009

(86) PCT No.: PCT/JP2009/066201
§ 371 (c)(1),
(2), (4) Date: Mar. 8, 2011

(87) PCT Pub. No.: WO2010/030036
PCT Pub. Date: Mar. 18, 2010

(65) Prior Publication Data
US 2011/0160493 A1    Jun. 30, 2011

(30) Foreign Application Priority Data
Sep. 11, 2008   (JP) .................... 2008-233587

(51) Int. Cl.
| | | |
|---|---|---|
| *B01J 23/00* | (2006.01) | |
| *B01J 23/02* | (2006.01) | |
| *B01J 23/06* | (2006.01) | |
| *B01J 23/70* | (2006.01) | |
| *B01J 23/72* | (2006.01) | |
| *C07C 27/00* | (2006.01) | |
| *C07C 29/00* | (2006.01) | |
| *C07C 31/18* | (2006.01) | |
| *C07C 51/36* | (2006.01) | |

(52) U.S. Cl.
USPC ........... 502/318; 502/300; 502/319; 502/331; 502/343; 502/345; 502/346; 568/852; 568/861; 554/141; 554/146

(58) Field of Classification Search
USPC ................ 502/318, 319, 331, 343, 345, 346; 568/852, 861; 554/141, 146
See application file for complete search history.

(56) References Cited

U.S. PATENT DOCUMENTS

| | | | | |
|---|---|---|---|---|
| 3,197,418 A | * | 7/1965 | Maebashi et al. ............. | 502/244 |
| 4,758,546 A | | 7/1988 | Baer et al. | |
| 4,801,574 A | | 1/1989 | Brown et al. | |
| 4,808,562 A | | 2/1989 | Kubersky et al. | |
| 4,918,248 A | * | 4/1990 | Hattori et al. ................. | 568/885 |
| 5,008,235 A | * | 4/1991 | Wegman et al. ............. | 502/342 |
| 5,229,346 A | | 7/1993 | Mori et al. | |
| 5,334,779 A | * | 8/1994 | Kuo ............................... | 568/864 |
| 5,403,962 A | | 4/1995 | Schneider et al. | |
| 5,481,048 A | * | 1/1996 | Tsukada et al. .............. | 568/885 |
| 5,554,574 A | * | 9/1996 | Tsukada et al. .............. | 502/345 |
| 5,658,843 A | | 8/1997 | Tsukada et al. | |
| 6,049,013 A | | 4/2000 | Ueoka et al. | |
| 6,410,806 B2 | * | 6/2002 | Oku et al. ..................... | 568/814 |
| 6,495,706 B2 | * | 12/2002 | Aoki et al. .................... | 554/146 |
| 8,188,321 B2 | * | 5/2012 | Suzuki et al. ................. | 568/861 |
| 8,258,351 B2 | * | 9/2012 | Suzuki et al. ................. | 568/852 |
| 2001/0016671 A1 | | 8/2001 | Oku et al. | |

FOREIGN PATENT DOCUMENTS

| | | |
|---|---|---|
| CA | 2226534 A1 | 7/1998 |
| CN | 1067191 A | 12/1992 |
| CN | 1116412 A | 2/1996 |
| JP | 61-161146 A | 7/1986 |
| JP | 5-177140 A | 7/1993 |
| JP | 5-293377 A | 11/1993 |
| JP | 6-36867 B2 | 5/1994 |
| JP | 8-9903 A | 4/1996 |
| JP | 10-245351 A | 9/1998 |
| JP | 10-265418 A | 10/1998 |
| JP | 2990568 B2 | 12/1999 |
| JP | 2000-93800 A | 4/2000 |
| JP | 2001-199917 A | 7/2001 |
| JP | 3195357 B2 | 8/2001 |

OTHER PUBLICATIONS

Notification of First Office Action for corresponding Chinese Patent Application No. 200980135822.8, dated Nov. 13, 2012.
International Search Report, dated Jan. 12, 2010, for Application No. PCT/JP2009/066201.
Vijayaraghavan et al., "In-Situ Activation of Methanol Synthesis Catalyst in a Three-Phase Slurry Reactor", Fuel Science & Technology Int'l, vol. 14, No. 6, pp. 729-738, 1996.
Notification of Second Office Action for corresponding Chinese Patent Application No. 200980135822.8, dated Jun. 20, 2013.

* cited by examiner

*Primary Examiner* — Patricia L Hailey
(74) *Attorney, Agent, or Firm* — Birch, Stewart, Kolasch & Birch, LLP

(57) ABSTRACT

The present invention provides the method for preparing a catalyst including the following steps 1 and 2, and the method for producing an alcohol including preparing a catalyst by the method and subjecting a carboxylic acid or a carboxylic acid ester to catalytic reduction with hydrogen in the presence of the prepared catalyst:

step 1: immersing a molded precursor of a catalyst containing metal oxide in a solvent, step 2: supplying hydrogen gas or a mixture of hydrogen gas with an inert gas to a catalyst layer in the presence of a solvent to reduce the catalyst precursor prepared in the step 1.

8 Claims, No Drawings

METHOD FOR PREPARING CATALYST

CROSS REFERENCE TO RELATED APPLICATIONS

This application is a National Phase application of PCT/JP2009/066201 filed on Sep. 10, 2009, which claims the benefit under 35 U.S.C. §119(a) to Patent Application No. 2008-233587 filed in Japan, on Sep. 11, 2008. The entire contents of all of the above applications are hereby incorporated, by reference.

FIELD OF THE INVENTION

The present invention relates to a method for preparing a catalyst and a method for producing an alcohol.

BACKGROUND OF THE INVENTION

For preparing catalysts, there have been various methods of reducing catalyst precursors containing metal oxides proposed. For example, a copper-based catalyst is used in production of an alcohol by hydrogenation of a carboxylic acid or a carboxylic acid ester. When a fixed-bed reaction system is employed, the copper-based catalyst is entirely subjected to gas phase reduction for activation. In industry, such gas phase reduction of a catalyst is generally carefully conducted at a predetermined temperature under an inert gas flow that contains several to several tens percent of hydrogen in order to avoid local overheat due to rapid reduction of the catalyst.

In some cases, reduction of a metal oxide with hydrogen generates a large amount of heat. For example, one mole of copper oxide generates 20 kcal of reduction heat. In addition, reduced copper is known to have very low thermal stability. Thus, it is important to gradually conduct reduction with controlling heat generation to produce a copper catalyst without impairing its performance. This is particularly important for a molded catalyst, because it has a difficulty of heat release.

Therefore, it is naturally expected for a catalyst subjected to reductive activation with high concentrate hydrogen for a short time in a gas phase to have significantly decreased catalytic performance due to rapid generation of heat, and more for a catalyst subjected to reductive activation for a short time in such a large scale as in industry to fall into very serious situations due to rapid elevation of temperature. As thus, a general method for practical gas phase reductive activation of a catalyst containing copper oxide is generally conducted with low concentrate hydrogen for a long time. For instance, JP-A 61-161146 describes that such reductive activation takes a time from 4 to 14 days.

As described above, fixed-bed reaction systems generally employ gas phase reduction, but some systems employ liquid phase reduction to activate a catalyst precursor containing copper oxide. For example, JP-B 2990568 discloses liquid phase reduction of a molded precursor of a copper-containing hydrogenation catalyst, that reduction is conducted at a temperature ranging from 50 to 140° C.

JP-B 3195357 discloses activation of a copper-containing hydrogenation catalyst by supplying a mixture of hydrogen with an inert gas under an inert solvent flow.

SUMMARY OF THE INVENTION

The present invention provides a method for preparing a catalyst, including the following steps 1 and 2:

step 1: immersing a molded precursor of a catalyst containing metal oxide in a solvent, step 2: supplying hydrogen gas or a mixture of hydrogen gas with an inert gas to a catalyst layer in the presence of a solvent to reduce the catalyst precursor prepared in the step 1.

The present invention also provides a method for producing an alcohol, including preparing a catalyst by the method of preparation, and subjecting a carboxylic acid or a carboxylic acid ester to catalytic reduction with hydrogen in the presence of the prepared catalyst.

The present invention also provides use of the catalyst prepared by the method of the present invention for producing an alcohol, including subjecting a carboxylic acid or a carboxylic acid ester to catalytic reduction with hydrogen.

DETAILED DESCRIPTION OF THE INVENTION

Even the method of JP-B 2990568 is insufficient for preparing a catalyst having higher activity, and there is still remaining a matter of study.

The present invention provides a method for preparing a catalyst having higher activity by liquid phase reduction, and a method for efficiently producing an alcohol.

According to the present invention, a catalyst having high activity can be prepared by liquid phase reduction, and a catalyst prepared by the method of the present invention can be used to produce an alcohol having high quality at high yield.

[Preparation of a Catalyst]

The method for preparing a catalyst of the present invention includes the steps 1 and 2.

The molded precursor of the catalyst containing a metal oxide used in the present invention is preferably a precursor of a copper-containing hydrogenation catalyst.

Examples of the precursor of the copper-containing hydrogenation catalyst include, but not particularly limited to, copper-chromium oxide, copper-zinc oxide, copper-iron oxide, copper-aluminum oxide, and copper-silica oxide. These precursors may be used alone or in combination of two or more. Among these precursors, preferred are copper-zinc oxides. Specific examples include CuO—ZnO— [an oxide of at least one metal selected from the group consisting of elements of groups IIa and IIIb of the Periodic Table, lanthanide, and actinide] described in paragraphs 0013 to 0014 of JP-A 5-177140.

A content of copper oxide in the precursor of the copper-containing hydrogenation catalyst is preferably 5 to 98% by weight, and more preferably 20 to 98% by weight of the total weight of the precursor. The precursor may be supported on a carrier such as a silica, an alumina, a zirconium oxide, a titanium oxide, and a silica-alumina carriers. In this case, the total weight of the precursor refers a weight including such a carrier.

In the present invention, a shape of the molded precursor can be arbitrary selected within the scope that does not interfere with an operation of a fixed-bed reactor. In general, the molded catalyst precursor preferably has a cylindrical shape produced by tableting or extrusion molding or a spherical particle shape having a size of 1 to 20 mm, because the catalyst precursor having such a shape can be easily produced at low cost.

In the present invention, it is important to perform first the step 1 of immersing the catalyst precursor in a solvent and second the step 2 of reducing the catalyst. It is possible by immersing the catalyst precursor in a solvent in advance to substitute the surface of the catalyst precursor to a liquid and prevent dry spots from generating. At a dry spot of the catalyst, gas phase reduction progresses to cause decrease of catalytic performance.

The solvent used in the step 1 preferably substantially does not cause elution or irreversible adsorption of the catalyst precursor or the catalyst and formation of a compound with the catalyst, and preferably has low concentration of catalyst poisons such as nitrogen compounds/sulfur compounds/phosphor compounds. Such a solvent is in the liquid state under the treatment conditions of reductive activation of the catalyst. Examples of the solvent include glyceride oils, esters, alcohols, and hydrocarbons. Preferred for the catalyst precursor used in production of an alcohol are glyceride oils, fatty acid esters, aliphatic alcohols, and hydrocarbons, that do not affect adversely on quality of the produced alcohol. These solvents may be used alone or in combination of two or more. Specific examples of the glyceride oil include mono-, di-, and triglycerides containing fatty acids having 6 to 22 carbon atoms. Examples of the fatty acid ester include esters of fatty acids having at least one fatty acid group having 2 to 22 carbon atoms with aliphatic alcohols having 1 to 22 carbon atoms. Examples of the aliphatic alcohol include those having 2 to 22 carbon atoms and at least one hydroxy group and being a liquid state under the conditions of a reductive activation of the catalyst. Examples of the hydrocarbon include liquid paraffin and cyclic hydrocarbons.

Other solvent may be used as long as a residual impurity derived from the solvent does not affect seriously the quality of a produced alcohol. Examples of such a solvent include ethers, aldehydes, and ketones, that are in the liquid state under the conditions of reductive activation of the catalyst. In these organic compounds including the former esters and alcohols, alkyl moieties include at least one of a linear chain, a branched chain, an aliphatic ring, and an aromatic ring.

In the step 1, the step of immersing the catalyst precursor in a solvent is not limited specifically. It is acceptable to immerse the catalyst precursor in a solvent in advance outside a reactor and then fill the reactor with the catalyst precursor. It is also acceptable to fill the reactor with the catalyst precursor and then supply a solvent to the reactor to immerse the catalyst precursor. The supply of the solvent to the reactor maybe performed from the top or the bottom of the filled catalyst precursor. In supply of the solvent, a feed rate of the solvent is preferably controlled such that the filled catalyst precursor does not float. From this viewpoint, the solvent is preferably supplied from the upper part of the catalyst precursor. The immersion of the catalyst precursor in a solvent can be performed with or without stirring and/or flowing. The immersion with no agitation is simpler in operation. In a preferred embodiment of a fixed-bed reaction system, first, the catalyst precursor is filled in a reactor, and then, a solvent is supplied to the reactor to fully immerse the catalyst precursor. Supply of and/or immersion with the solvent may be performed under the atmospheric pressure or by degassing the reactor at the decompression conditions according to need. From the viewpoint of adequate replacement of gas and liquid, a time of immersion of the catalyst precursor is preferably not less than 0.5 hours, and more preferably not less than 1 hour. The upper limit of the time of immersion is not technically limited, but preferably not more than 50 hours, more preferably not more than 30 hours, and even more preferably not more than 10 hours, from the viewpoint of work efficiency.

After the immersion, the solvent is removed from the reactor. In or after removing, an inert gas such as nitrogen is preferably supplied to the reactor to replace the inner atmosphere of the reactor for preparing for reduction of the catalyst precursor. This replacement generally results in removing off fine powder of the catalyst precursor generated by operations such as filling the catalyst precursor together with the solvent out to the reactor. As thus, the step 1 of the present invention contributes also to prevention of contamination of a catalyst in a reaction product. Of course, the reactor can be further supplied with a solvent or an inert gas to remove fine powder of the catalyst precursor.

In the step 2 of the present invention, the catalyst precursor prepared in the step 1 is reduced in the presence of a solvent. The solvent used in the step 2 may be the same or different to the solvent used in the step 1. From the viewpoint of simple operation, the same solvent is preferably used.

From the viewpoint of providing a uniform wet state of the catalyst with the solvent and preventing gas phase reduction of a part of the catalyst, a flow rate of the solvent in the step 2 is preferably a liquid hourly space velocity of not less than 0.1 $[Hr^{-1}]$. The upper limit is not specifically limited, but preferably not more than 5.0 $[Hr^{-1}]$, and more preferably not more than 3.0 $[Hr^{-1}]$, from the economic viewpoint. For starting reduction of the catalyst under conditions as mild as possible, in introducing the solvent to the reactor, a temperature is preferably 20 to 60° C. and increased to the temperature for reductive activation described below.

In the step 2, reduction of the catalyst precursor is performed by supplying hydrogen gas or a mixture of hydrogen gas with an inert gas as a reductant and contacting it with the catalyst precursor. As the inert gas for diluting hydrogen, nitrogen, helium, argon, methane, and the like can be used. In the gas, a concentration of hydrogen is preferably 2 to 100% by volume, and more preferably 5 to 100% by volume. Considering a time taking to the reductive activation, a concentration of hydrogen is preferably set such that a hydrogen partial pressure is not less than one atmosphere.

Supply of the gas is preferably conducted under the atmospheric pressure to 30 MPa (300 atmospheres) in the presence of a solvent. Although the effects of the present invention can be achieved under a pressure over 30 MPa, such a condition puts heavy load on facilities. From the economic viewpoint, the pressure condition is preferably not more than 30 MPa.

From the viewpoints of providing a good heat-removing effect and removing effectively water produced in the reduction to achieve sufficient catalytic properties, supply of the gas is preferably a gas hourly space velocity of not less than 50 $[Hr^{-1}]$, and more preferably not less than 100 $[Hr^{-1}]$. From the viewpoint of facilities, the gas hourly space velocity is preferably not more than 10000 $[Hr^{-1}]$, and more preferably not more than 5000 $[Hr^{-1}]$. From the same reason in introduction of the solvent, in introducing the gas, a temperature is generally 20 to 60° C. and increased to the temperature for reductive activation.

In the present invention, the liquid phase reduction is performed with flowing the solvent and supplying the gas at the reductive activation temperature ranging from 50 to 200° C.

The liquid phase reduction of the catalyst precursor may be performed at a main steady temperature, or during increasing a temperature, or under conditions including both states. An increasing pattern of temperature may be continuous or discontinuous, and an increasing rate of temperature needs not to be constant. The liquid phase reduction thus can be performed at any increasing pattern of temperature including a steady temperature and various increasing rates without any problems.

From the viewpoint of sufficient progress of reductive activation, a time of the liquid phase reduction, which may be varied according to conditions of temperature described above, is preferably not less than 1.5 hours, and more preferably not less than 6 hours in general. From the economic viewpoint, the time is preferably not more than 100 hours.

In the increasing pattern of temperature, from the viewpoint of preventing elongation of the time taking to conduct reductive activation of the catalyst precursor, an increasing rate of temperature is preferably not less than 0.5° C./Hr, more preferably not less than 1° C./Hr, and even more preferably not less than 5° C./Hr. From the viewpoint of preventing rapid increase of temperature due to accumulation of reduction heat accompanied with rapid reduction of the catalyst to easily control the reduction, the increasing rate is preferably not more than 40° C./Hr, more preferably not more than 30° C./Hr, and even more preferably not more than 20° C./Hr.

The catalyst prepared by the method of the present invention can be used in a fixed bed continuous reaction process mainly to produce an alcohol and to conduct various hydrogenations such as hydrogenation of an aldehyde or ketone group, hydrogenation of olefins, and hydrogenation of a nitro group. As thus, preparation of the catalyst of the present invention is preferably conducted in a reactor for a fixed bed continuous reaction, because the resultant activated catalyst can be used as is to an intended use such as production of an alcohol.

[Method for Producing an Alcohol]

The method for producing an alcohol of the present invention includes subjecting a carboxylic acid or a carboxylic acid ester to catalytic reduction with hydrogen in the presence of the catalyst prepared by the method of the present invention.

Examples of the carboxylic acid of a raw material include natural animal and vegetable fatty acids obtained from such as coconut oil, palm kernel oil, palm oil, beef tallow, and lard, and synthetic fatty acids. Examples of the carboxylic acid ester desirably include esters of oil-and-fat and fatty acids. Examples of the oil-and-fat include mono-, di-, and triglycerides composed of saturated and unsaturated fatty acids having 6 to 22 carbon atoms. Examples of the fatty acid ester include linear, branched and unsaturated fatty acid esters having at least one carbon atom and at least one ester group. Specific examples of the fatty acid ester include formates, acetates, caproates, caprylates, caprates, undecenoates, laurates, myristates, palmitates, stearates, isostearates, oleates, arachates, behenates, oxalates, maleates, adipates, and sebacates. An alcohol moiety that constitutes the fatty acid ester is not specifically limited to, but preferably has an aliphatic alcohol having 1 to 22 carbon atoms. An ester to be subjected to hydrogenation in the present invention is not specifically limited to the fatty acid ester, and may be selected from alicyclic carboxylates such as cyclohexanecarboxylates, benzoates, and phthalates, and aromatic carboxylates, and derivatives thereof without any problems.

In the present invention, for hydrogenating the carboxylic acid or the carboxylic acid ester, a fixed-bed continuous reaction process is preferably employed. Hydrogenation can be conducted in a solvent, but desirably without a solvent, considering productivity. When a solvent is used, it is selected from those that do not adversely affect the reaction, including alcohols, dioxanes, or paraffins. A reaction temperature is preferably 130 to 300° C., and more preferably 160 to 250° C. A reaction pressure is preferably 0.0098 to 29 MPa (0.1 to 300 kg/cm$^2$). A liquid hourly space velocity in supplying a raw material, which is appropriately determined according to reaction conditions, is preferably within the range of 0.2 to 5.0 [Hr$^{-1}$], considering productivity or reactivity.

EXAMPLES

The following Examples demonstrate the present invention. Examples are intended to illustrate the present invention and not to limit the present invention.

Example 1

According to a method described in Example 5 of JP-A 5-177140, a catalyst precursor containing CuO, ZnO, and BaO supported on TiO$_2$ was prepared. The resultant precursor powder was formed into a cylindrical tablet and baked for two hours at 400° C. to give a molded precursor of a catalyst having a diameter of 3 mm and a height of 3 mm and the following composition by weight:

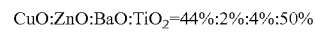

$CuO:ZnO:BaO:TiO_2=44\%:2\%:4\%:50\%$ 480 cc of the molded precursor of the catalyst thus obtained was filled in a fixed bed high-pressure flow reactor. Then, to this was supplied 500 cc of lauryl alcohol (Kao Corporation, trade name: KALCOL-20, purity: 99.8%) from the top of the reactor to immerse the molded precursor of catalyst in lauryl alcohol for one hour. After the immersion treatment, lauryl alcohol was taken off, and the inner atmosphere of the reactor was replaced with nitrogen.

Then, liquid phase reduction was performed as follows. At a temperature of 40° C., a mixed gas containing hydrogen and nitrogen at concentrations of 50% by volume and 50% by volume respectively was introduced at a gas flow rate of 65 NL/Hr, and then lauryl alcohol (Kao Corporation, trade name: KALCOL-20, purity: 99.8%) was passed through the reactor at a flow rate of 240 cc/Hr. After flow rates of the liquid and the gas were stabilized, a temperature of the reactor was increased at a rate of 10° C./Hr to 100° C., hold at the temperature for 55 hours, and then increased at a rate of 10° C./Hr to 200° C., and hold at the temperature for 6 hours, under a pressure of 20 kg/cm$^2$ (gauge pressure) to conduct the reduction treatment of the catalyst precursor.

After ended reductive activation of the catalyst precursor, lauryl alcohol was changed to fatty acid methyl ester (saponification value: 243) having a distribution of chain length of 8 to 18 carbon atoms. Under conditions of a reaction temperature of 220° C., a reaction pressure of 200 kg/cm$^2$, a liquid hourly space velocity of 1.0 [Hr$^{-1}$], and a flow rate of hydrogen of 25 times by mole to fatty acid methyl ester, hydrogenation was conducted. A catalytic activity was determined as a first-order rate constant for the reaction per unit volume of the molded catalyst. Results are shown in Table 1.

In Example 1, an alcohol can be efficiently produced with the catalyst having high catalytic activity. Further, the alcohol produced by hydrogenation had high quality.

Comparative Example 1

Liquid phase reduction and hydrogenation of fatty acid methyl ester were similarly performed to in Example 1, except that immersion of a molded precursor of a catalyst in lauryl alcohol was not performed. The results are shown in Table 1.

In Comparative Example 1, quality of the alcohol produced by hydrogenation was equal to that in Example 1, but productivity of the alcohol was lower than that in Example 1 due to low activity of the catalyst.

TABLE 1

| | | Example 1 | Comparative example 1 |
|---|---|---|---|
| Step 1 | | immersing a catalyst precursor in K-20*¹ for one hour | — |
| Condition of reductive activation of catalyst | | | |
| Solvent | [—] | K-20*¹ | K-20*¹ |
| LHSV*² | [HR⁻¹] | 0.5 | 0.5 |
| Pressure | [kg/cm²] | 20 | 20 |
| Concentration of hydrogen | [% by volume] | 50 | 50 |
| Catalyst performance | | | |
| Relative activity*³ | [—] | 132 | 100 |

*¹KALCOL-20(lauryl alocohol purity: 99.8%, Kao Corporation)
*²liquid hourly space velocity of a solvent
*³relative value based on activity of Comparative Example 1 set to 100

The invention claimed is:

1. A method for preparing a catalyst, comprising the following steps 1 and 2:
   step 1: immersing a molded precursor of a catalyst containing a metal oxide in a solvent and preventing dry spots from generating on a surface of the molded precursor,
   step 2: supplying hydrogen gas or a mixture of hydrogen gas with an inert gas to a catalyst layer in the presence of a solvent to reduce the catalyst precursor prepared in the step 1.

2. The method for preparing a catalyst according to claim 1, wherein the solvent is at least one selected from the group consisting of glyceride oils, fatty acid esters, aliphatic alcohols, and hydrocarbons.

3. The method for preparing a catalyst according to claim 1, wherein the catalyst is a copper-containing hydrogenation catalyst.

4. The method for preparing a catalyst according to claim 3, wherein the copper-containing hydrogenation catalyst is at least one selected from the group consisting of copper-chromium oxide, copper-zinc oxide, copper-iron oxide, copper-aluminum oxide and copper-silica oxide.

5. The method for preparing a catalyst according to any of claim 1 or 2, wherein the catalyst precursor is immersed in the solvent for 0.5 to 50 hours.

6. A method for producing an alcohol, comprising preparing a catalyst by the method according to claim 1 or 2, and subjecting a carboxylic or a carboxylic acid ester to a catalytic reduction with hydrogen in the presence of the prepared catalyst.

7. The method for preparing a catalyst according to any of claim 1 or 2, in which step 1 is conducted in a fixed-bed reactor and step 2 is conducted while flowing the solvent and supplying the gas.

8. The method for preparing a catalyst according to claim 7, wherein step 1 comprises filling the fixed-bed reactor with a molded precursor containing a metal oxide, then supplying the solvent, immersing the molded precursor with the solvent and removing the solvent from the reactor.

* * * * *